(12) United States Patent
Sullivan et al.

(10) Patent No.: US 9,445,762 B2
(45) Date of Patent: Sep. 20, 2016

(54) FULLY SELF-CONTAINED UNIT DOSE DEVICES FOR ALLERGY SKIN TESTING

(71) Applicant: Mystic Pharmaceuticals, Inc., Cedar Park, TX (US)

(72) Inventors: Timothy R Sullivan, Austin, TX (US); Jeff Gjertsen, Austin, TX (US); Jesse Hancock, Cedar Park, TX (US)

(73) Assignee: Mystic Pharmaceuticals, Inc., Austin, TX (US)

( * ) Notice: Subject to any disclaimer, the term of this patent is extended or adjusted under 35 U.S.C. 154(b) by 0 days.

(21) Appl. No.: 14/012,821

(22) Filed: Aug. 28, 2013

(65) Prior Publication Data

US 2015/0126898 A1    May 7, 2015

Related U.S. Application Data

(60) Provisional application No. 61/695,202, filed on Aug. 30, 2012.

(51) Int. Cl.
*A61B 5/00* (2006.01)

(52) U.S. Cl.
CPC ............ *A61B 5/411* (2013.01); *A61B 5/6848* (2013.01); *G01N 2800/24* (2013.01)

(58) Field of Classification Search
CPC ............................ A61B 10/0035; A61B 5/411
USPC ........................................................ 600/556
See application file for complete search history.

(56) References Cited

U.S. PATENT DOCUMENTS

| | | | |
|---|---|---|---|
| 2,893,392 A * | 7/1959 | Wagner | A61B 17/205 206/222 |
| 3,556,080 A | 1/1971 | Hein | |
| 3,703,890 A | 11/1972 | Saunders | |
| 5,076,282 A | 12/1991 | Fishman et al. | |
| 5,099,857 A * | 3/1992 | Baldo et al. | 600/556 |
| 5,335,670 A | 8/1994 | Fishman | |
| 6,447,482 B1 * | 9/2002 | Rønborg et al. | 604/131 |
| 6,656,147 B1 * | 12/2003 | Gertsek | A61M 5/14248 604/185 |
| 2002/0092524 A1 * | 7/2002 | Lockhart | A61M 15/0028 128/203.21 |
| 2005/0000514 A1 * | 1/2005 | Sullivan | A61M 15/0028 128/200.24 |
| 2006/0011666 A1 * | 1/2006 | Wurtz | B65D 1/095 222/541.1 |
| 2006/0169278 A1 * | 8/2006 | Djupesland | A61M 15/0028 128/200.14 |
| 2006/0213509 A1 * | 9/2006 | Marin | A61B 18/0218 128/200.23 |

(Continued)

OTHER PUBLICATIONS

International Search Report of PCT Application No. PCT/US2013/57751 date of mailing Nov. 15, 2013: pp. 1-2.

(Continued)

*Primary Examiner* — Michael C Stout (57) ABSTRACT

The present invention discloses a system for applying antigens or other diagnostic substances to the skin of a subject for allergy testing. The system is comprised of fully contained predetermined quantities of antigenic or other testing material contained in sealed unit doses that maintain sterility and provide for precise handling and administration. Each unit dose contains an internal mechanism. The mechanism provides for piercing the laminate and comprises an internal channel for fluid communication, and may have an abrasive protrusions at the tip for piercing or abrading the skin surface to aid in generating a diagnostic response. The unit dose or doses may be housed in devices that provide for administration of the test material to the subject wherein the applicator section may contain protrusions for piercing or abrading the skin of a subject.

8 Claims, 8 Drawing Sheets

(56) References Cited

U.S. PATENT DOCUMENTS

| | | | | |
|---|---|---|---|---|
| 2006/0239860 | A1* | 10/2006 | Evers | B01F 11/0071 422/400 |
| 2006/0259006 | A1* | 11/2006 | McKay | A61B 17/3478 604/506 |
| 2008/0177246 | A1* | 7/2008 | Sullivan | A61M 11/002 604/520 |
| 2008/0214952 | A1* | 9/2008 | Mir et al. | 600/556 |
| 2008/0283439 | A1* | 11/2008 | Sullivan | A61M 15/0028 206/531 |
| 2009/0099478 | A1* | 4/2009 | Cassells | A61B 5/1411 600/583 |
| 2010/0022910 | A1* | 1/2010 | Lane | A61B 5/0059 600/556 |
| 2010/0100005 | A1* | 4/2010 | Mir et al. | 600/556 |
| 2010/0217206 | A1* | 8/2010 | Lum | A61M 5/348 604/240 |
| 2011/0270220 | A1* | 11/2011 | Genosar | A61J 1/067 604/506 |
| 2012/0123297 | A1* | 5/2012 | Brancazio | A61B 5/1411 600/576 |
| 2012/0157964 | A1* | 6/2012 | Haimi | A61M 5/2053 604/506 |
| 2012/0219347 | A1* | 8/2012 | Law et al. | 401/133 |
| 2012/0259277 | A1* | 10/2012 | Shay | A61M 15/0028 604/58 |
| 2013/0211350 | A1* | 8/2013 | Bayly | A61M 35/003 604/290 |

OTHER PUBLICATIONS

Written Opinion of PCT Application No. PCT/US2013/57751 date of mailing Nov. 15, 2013, pp. 1-5.

* cited by examiner

FULLY SELF-CONTAINED UNIT DOSE DEVICES FOR ALLERGY SKIN TESTING

CROSS-REFERENCE TO RELATED APPLICATIONS

The present application claims benefit of priority under 35 U.S.C. §119(e) to U.S. Provisional Application 61/696,202 filed Sep. 2, 2012, the entire content of which is incorporated herein by reference for all purposes.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

FIELD OF THE INVENTION

Devices, systems and methods for the testing of medical conditions in humans and non-human animals whereby the systems provided are used to package and administer one or more allergens (or antigens) to the skin to assess the level of allergic reaction by the subject.

BACKGROUND OF THE INVENTION

Skin tests for allergic disorders were first described in 1867 and quickly evolved into the scratch test, which was initially used to confirm the diagnosis of food allergy in children. Methods used for allergy skin testing may be performed using either prick or puncture (percutaneous) or intradermal (intracutaneous) techniques. In clinical practice, the scratch has given rise to the prick or puncture test, and in some cases if the results are interpreted as negative, it is followed by the intradermal test. Intradermal testing is more sensitive than prick or puncture testing, and as a result, the extract for prick or puncture testing must be at least 1,000-fold more concentrated to achieve a similar level of sensitivity. Although intradermal may be more reproducible than prick or puncture testing, there are many factors that favor the routine use of the prick or puncture test for allergy testing. These factors include economy of time, patient comfort, and safety.

Allergy skin testing is minimally invasive and when performed correctly has good reproducibility. It is also preferred because the test results are available within minutes of the test application, enabling the physician to quickly devise an appropriate treatment plan on the initial consultation. Skin testing is easily quantifiable and can allow the evaluation of multiple allergens in a single session. There are a variety of factors that can influence or confound the allergy skin test procedure. These factors include type of skin testing, applicator device used, placement of tests (location and adjacent testing), the quality of the extracts used, and the potential confounding effects of medication. The technique of the technician administering the skin test can also directly influence the results.

Prick or puncture (percutaneous) tests are performed with either a single or multi-test applicator device. The applicator is dipped into a tray containing wells that have been filled by the clinician with the allergen extracts. Each well is typically filled with approximately 500 or more microliters of the allergen extract and there may be as many as 48 or more individual wells each containing a different extract. The technician dips the applicator into the tray wells to place a consistent amount of allergen extract on the applicator. The applicator is pressed against the skin and punctures the skin approximately one millimeter and administers the extract by contact. It is important that the technician achieve consistency in the administering the extract at each individual site. The tray containing the extracts may be used to test as many as twenty five subjects before it is refilled. Proper clinical handling procedure is to cover and place the tray containing the unused extracts in refrigerated storage in between testing procedures to prevent loss of potency, contamination and cross contamination of the extracts.

SUMMARY OF THE INVENTION

Various embodiments of the present invention provide for a skin testing system. The system includes both single and multi-test percutaneous applicator devices each containing a sterile unit dose blister comprised of a multi-layer flexible aluminum film laminate, an internal polymeric piercing nozzle device and a precise single dose of the allergen extract in each blister. The blisters are comprised of a pharmaceutical grade laminate that is composed of aluminum foil and polymeric resins.

According to an exemplary embodiment, a system is provided that includes unit dose blisters containing the compound to be administered mounted in an application housing configured to contain single or multiple compound containing blisters. The blister further comprises an internal piercing mechanism with a hollow channel. The internal piercing mechanism punctures the blister lidding material upon compression of the blister in the device and its internal channel further provides a channel for delivery of the compound of interest. Once expressed, the material passes through a hollow applicator tip the end of which includes one or more points or protrusions to abrade, pierce or puncture the subject's skin.

In yet another exemplary embodiment, the points or protrusions that abrade, pierce, or puncture the subject's skin are located on the internal piercing mechanism that is contained within the compound containing blister. In this embodiment, the application device need not have a hollow applicator tip since the skin abrasion is conducted by the internal piercing mechanism during compression and piercing of the blister.

This system eliminates the need for handling, filling and storing multiple tray wells with different extract (s) that are in close proximity to one another. Unit dose packaging and dispensing of the extracts enables a precise unit dose for each administration, maintains the potency and sterility of the extract until the point of administration, reduces the risk of cross contamination, simplifies the testing procedure and reduces the time required to complete the procedure for the clinician.

DETAILED DESCRIPTION OF THE PRESENT INVENTION

The following description of the exemplary embodiments refers to the accompanying drawings. The same reference numbers in different drawings identify the same or similar elements. The following detailed description does not limit the invention. Instead, the scope of the invention is defined by the appended claims. The following embodiments describe an apparatus and system for the administration of skin testing compounds to a subject.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

The present invention provides fully self-contained devices for surface, sub percutaneous, percutaneous, or sub dermal administration of a chemical, biochemical, or biologic material such as but not limited to an antigenic compound formulated as a fluid, powder or encapsulated gel, paste or other morphology suitable for administration to a human or non-human subject for the purpose of allergy testing or diagnostics, as well as administration of a therapeutic agents, e.g. a vaccine, monoclonal antibody, or other medicinal compound.

Figure 1A:
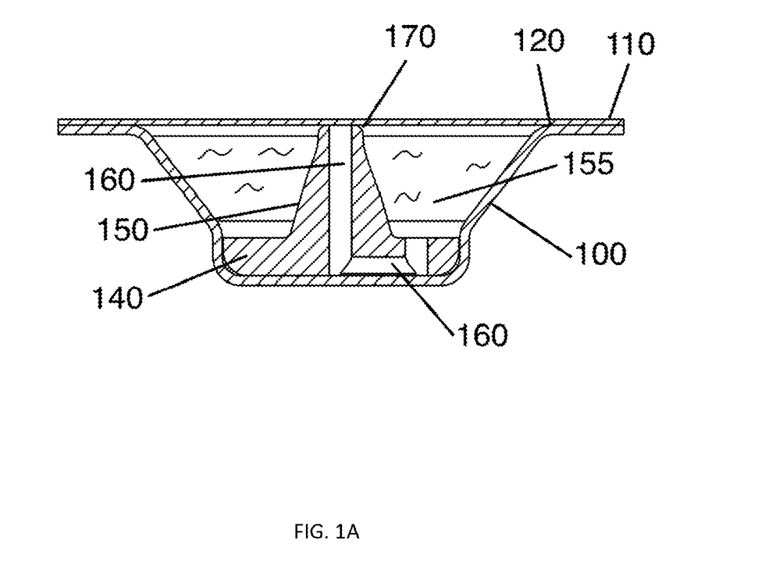
FIGS. 1A and 1B provide cutaway views of two preferred embodiments illustrating blisters with internal piercing mechanisms without (A) and with (B) abrasive tips.
Figure 1B:
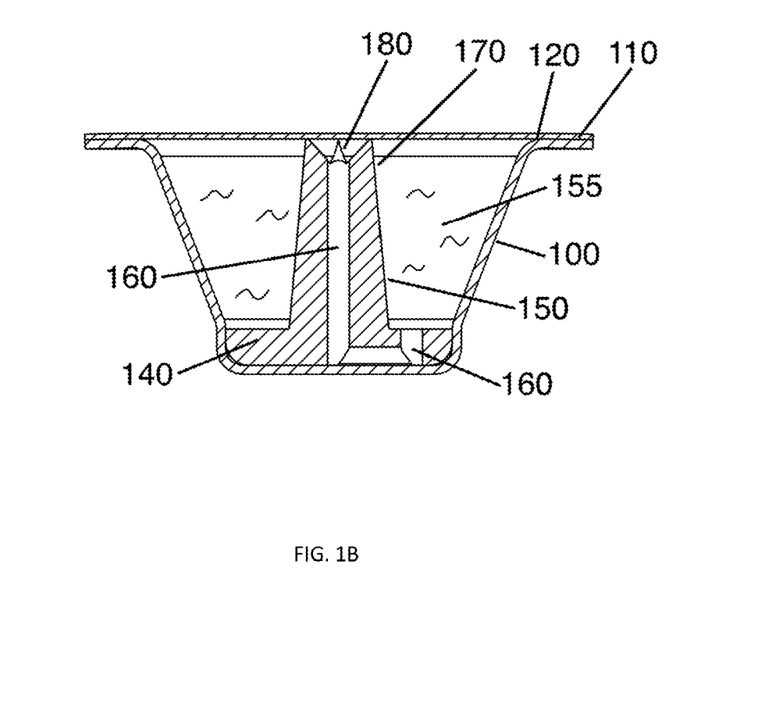

FIGS. 1A and 1B provide two preferred embodiments of blisters with internal piercing mechanisms without (A) and with (B) abrasive tips. In FIG. 1A the formed blister main body 100 formed as described below, for example, from polymer-metallic laminates sealed typically with a lidstock 110 material of the same of similar composition as the blister main body, and attached for example by thermal welding at a circle given as location 120, thereby forming a fully self-contained volume suitable for storage and delivery of quantities of liquids, suspensions, gels, pastes or even powders.

Integral to the invention is the unit dose blister formed from sheets of laminated material that may be comprised of metals, such as aluminum, with one or more adhered, bonded or adjacent layers of polymeric, cellulosic, or other singular or compounded material, or substance known in the art to be suitable for the forming, filling, and sealing of pharmaceuticals, chemicals, and biologics. Typically, said blisters are formed in a continuous web handling apparatus, with dosages of fluid or powder or other materials precisely metered into the formed cavity. Prior to or following filling, the internal piercing mechanism 140 is mechanically placed within the formed blister. Once filled and the internal mechanism placed, the blister is sealed with a lidstock material of the same or similar material as the base material either by the use of thermal or ultrasonic welding, or adhesives, or other means suitable for the sealing of pharmaceutical grade formed laminate containers known in the art.

Combined, the process is often referred to as "Form-Fill-Seal", or "FFS"; the products and process details of which are disclosed in multiple US patents including but not limited to U.S. Pat. Nos. 7,669,597, 8,047,204, and 7,963,089, as well as US applications, including but limited to US Application Publication 2011/0247305A1; all of which are incorporated herein by reference in their entirety.

The internal piercing mechanism may be formed from metallic or composite materials, but in preferred embodiment is comprised of any of various polymers, for example, polyethylene, PTFE, polypropylene, or others to include high purity, low leaching medical grade polymers known in the art of medical device and sterile packaging. The part in particular embodiment may be typically formed by for example, by machining, or preferably by injection or other molding processes known in the art. It is comprised of a base 140 and elongated tip 150. A channel to allow for fluid communication of the blister contents 155 to the blister exterior is given as 160. The channel may typically be formed during the injection molding process and maintain contain additional features such as ribs, flutes, spirals, restrictions, or diverging nozzle features to impart a particular dispense characteristic such as a spray, drop or narrow stream. The internal diameter and features may be designed by those skilled in the art of nozzle or spray system design of liquids and powders to produce a desired velocity, dispense time, pressure, or spray path.

When the blister is compressed by manual, electromechanical or pneumatic means, the tip 170 of the internal piercing mechanism punctures the lidstock 110 and pressurizes the blister contents. The piercing mechanism's internal channel 160 then allows the communication of the blister contents once the lidstock 110 is breached to the exterior. In FIG. 1A, the internal piercing mechanism tip 170 shown provides a narrowed diameter to facilitate the puncturing of the lidstock 110. The tip however may contain a number of design features to provide for specific lidstock piercing characteristics, for example, to reduce the lidstock "flap" formation as detailed in the commonly assigned patent application, "Piercing Device for Drug Delivery Systems," of US Patent Publication US2012-0310176-A1, which is incorporated herein by reference in its entirety.

Figure 2A:
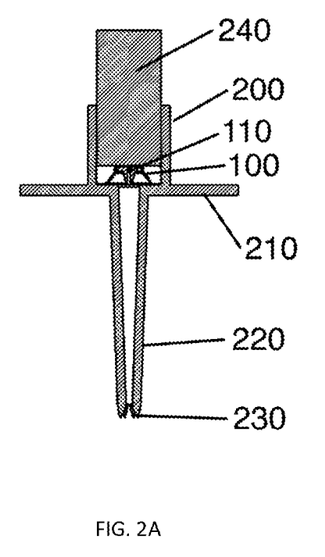
FIGS. 2A and 2B provide an exemplary single dose device whereby the internal piercing mechanism forms a cone or nozzle that is designed to pierce the blister from the inside upon being crushed in order to dispense a precise dose of the extract through the piercing mechanism. The dispensed antigen or other diagnostic material exits the blister through the piecing nozzle and travels through applicator to the percutaneous tip which pierces the skin and administers the antigen.
Figure 2B:
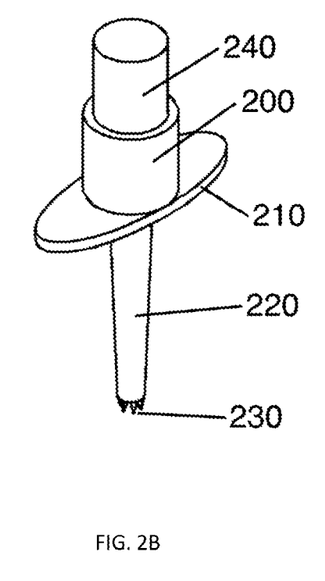
Figure 3:
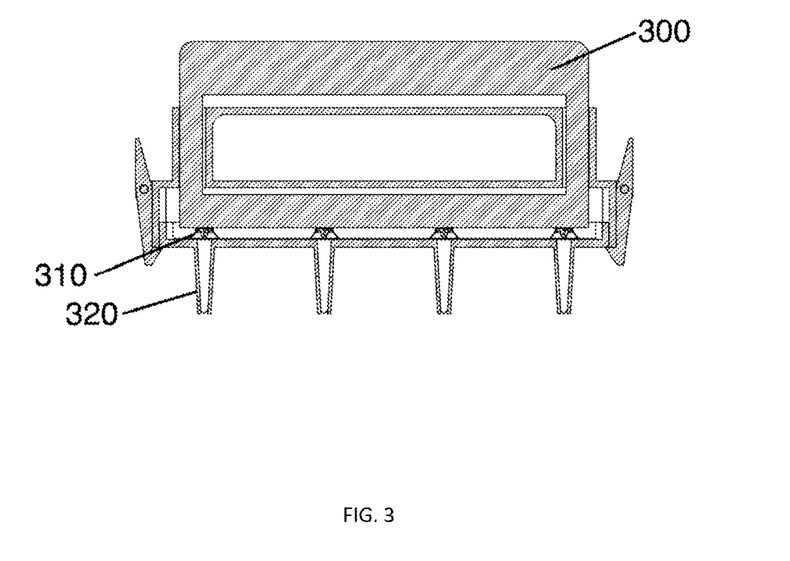
FIG. 3 illustrates an exemplary embodiment of a multi-dose device comprised of internally pierced unit doses with abrasive tipped applicators.

In certain preferred embodiments of the present invention, the internal piercing mechanism tip 170 as shown in FIG. 2B includes one or more sharpened or pointed protrusions 180.

Figure 4A:
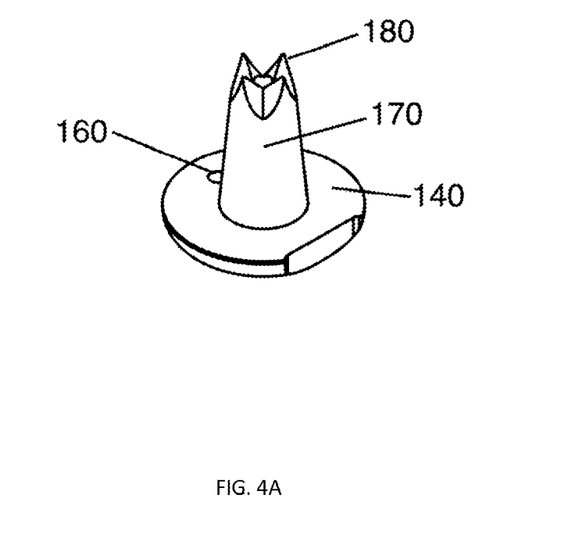
FIGS. 4A and 4B provide an exemplary internal piercing mechanism with an abrasive tip and an exemplary single dose device that dispenses the antigen or other diagnostic material out of the blister through the piecing mechanism that includes an internal fluid communication channel with abrasive tip that punctures the skin in order to directly administer the extract to the subject.
Figure 4B:
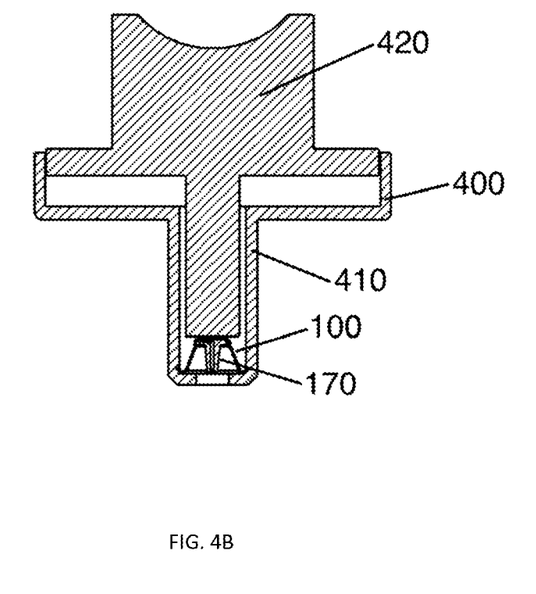
Figure 5A:
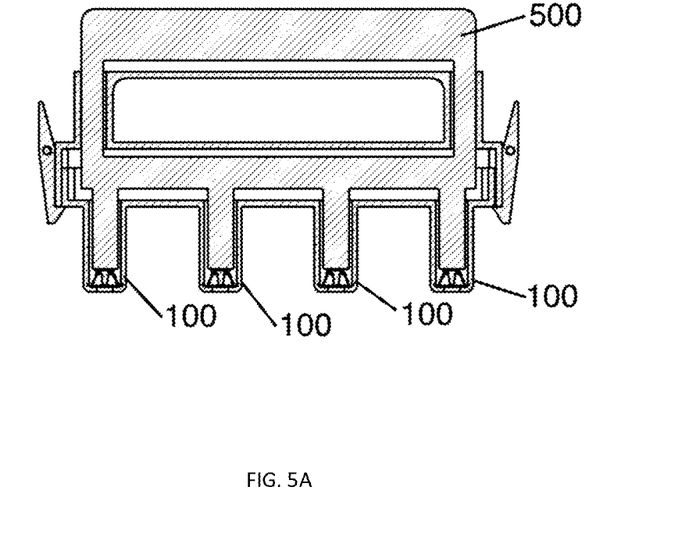
FIGS. 5A and 5B illustrates an exemplary embodiment of a multi-dose device comprised of multiple unit doses with abrasive tipped internally piercing mechanisms and a blowup of the end of a single applicator body of this device type.
Figure 5B:
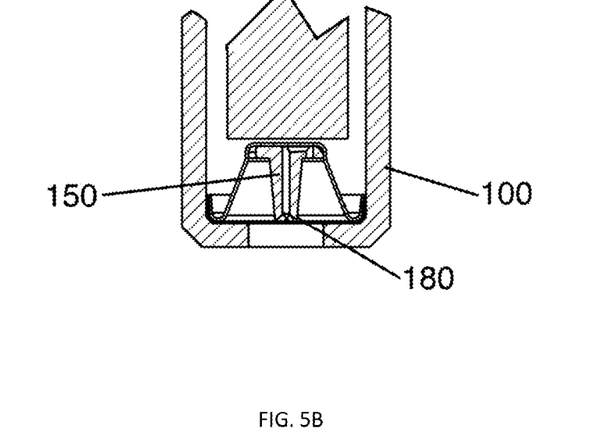
Figure 6:
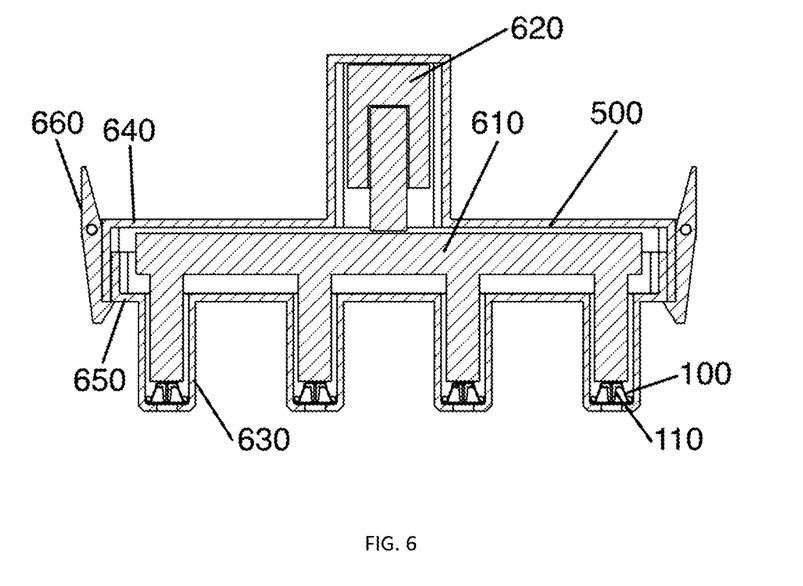
FIG. 6 gives an exemplary embodiment of a non-manually actuated device.
Figure 7A:
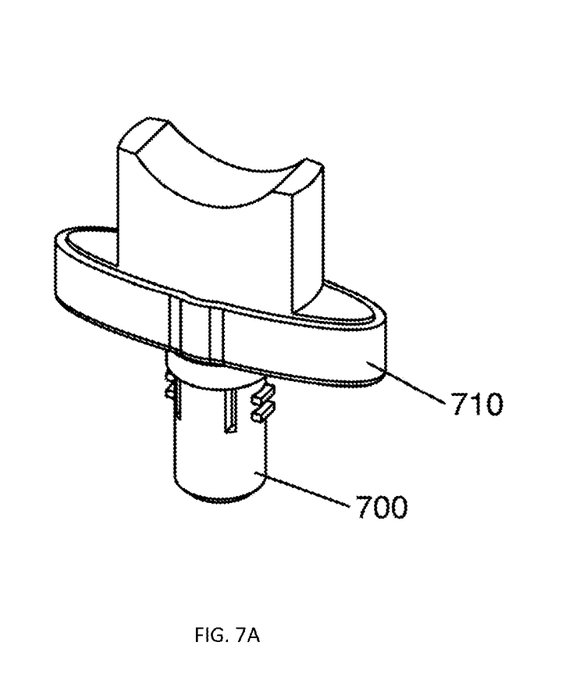
FIGS. 7A and B provide two views of a further exemplary embodiment of a reusable single dose device with replaceable applicator tip.
Figure 7B:
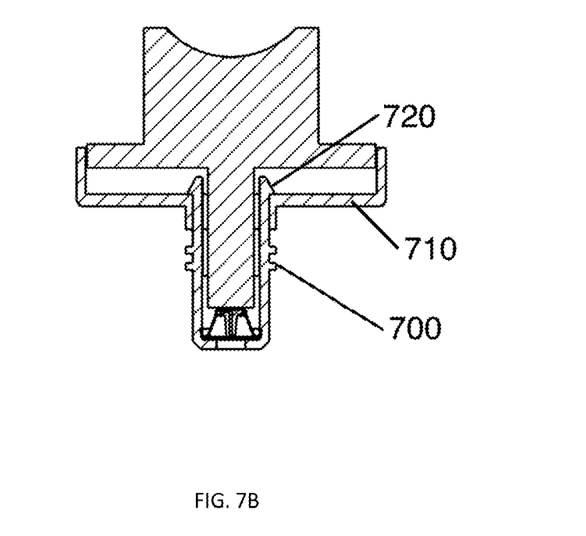
Figure 8:
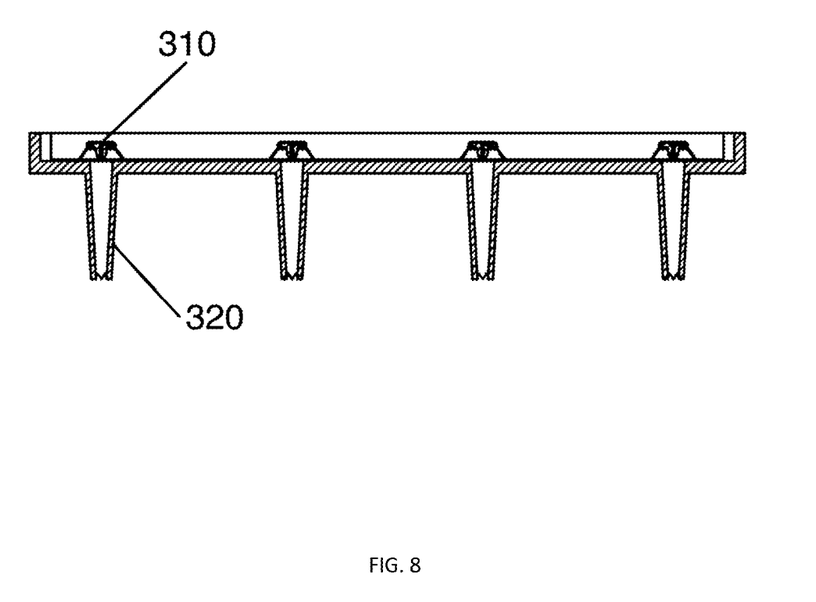
FIG. 8 provides a further exemplary embodiment of a reusable multiple dose device with replaceable applicator tip.

These tips contact the skin upon expression of the blister and provide for abrasion of the skin to facilitate the subject's skin reaction to the test material administered. (See also FIGS. 4A and 4B discussed below.)

FIGS. 2A and 2b provide two views of one exemplary embodiment of a self-contained device 200 that houses the antigen or other diagnostic material contained in the sealed unit dosage 100 form that also contains an internal piercing mechanism 110. The dosage form or blister is fixed or mounted to one end of the main single piece body 210 that elongates to a tapered applicator tip 220 with one or more sharp tips 230 on the distal most end of the tube opposite the internally piercing blister 100. The internally pierced blister is compressed by a piston, plunger or other mechanically levered force providing means 240, which causes the internal piercing mechanism 110 to puncture the sealed lidding material of the unit dose form blister 100 and ejects the antigen test material which passes through the applicator tip and contacts the subject's skin abraded by the scarring tips of 230. Once pierced, the dispensed material from the blister flows through the elongated applicator tip to the exit orifice aided by the pressure of the dispense and gravity. In this particular embodiment, the internal piercing mechanism 110 need not contain the abraded protrusions since they are provided by the elongated applicator tip 220.

The unit doses described in FIGS. 1A and 1B may also be configured into an array of formed blisters arranged in vectors or X and Y configured grids, circles, strips, cartridges, or other geometric arrangements that are subsequently loaded into a multi-unit dose, or multi-antigen dispenser device to provide for multiple tests to be performed within one operation. In this exemplary embodiment, shown conceptually in FIG. 3, a piston, plunger, levered plate or other force application means 300 that may be, by example, either mechanical, pneumatic or electromechanical in nature may be used to actuate one or more unit doses 310 either individually, sequentially, or substantially simultaneously. The individual devices may further be configured in a variety of housings, comprised of molded or machined parts, plates, bodies or enclosures of one or more parts and componentry known to those of ordinary skill in the art of device design to; for example, provide for system modularity such that the abrasive tipped applicators 320 can be changed out or sterilized between administrations, or to provide for ease of installing separate sheets or arrays of unit dose forms in the form of sheets, webs, strips, rolls or cartridges, or other design elements advantageous to form, function, or operation of the device.

In certain preferred embodiments of devices, the internal piercing mechanism 100 as shown in FIG. 1B contains one or more substantially pointed protrusions for the purpose of providing the piercing, pricking, scaring, puncturing, abrading or disturbance of the skin surface or one or more layers comprising the skin surface. Referring to FIGS. 4A and 4B, an exemplary embodiment is depicted providing the abrasive tipped internal piercing mechanism 170 that is contained within the sealed unit dose form or blister 100 (See FIGS. 1A and 1*b*) containing the antigenic or other diagnostic agents. In certain other preferred embodiments, the number, depth, sharpness, or angle of protrusions 180 may be tailored or engineered to provide a variable degree of abrasiveness or penetration of the skin surface. Such engineered factors are for the purpose of tailoring the depth of antigen penetration, which may be a factor in alleviating poor response reproducibility and accuracy known to exist in the field of skin allergy testing. Hence, FIG. 4B illustrates an exemplary single dose device 400 containing and employing said abrasive tipped internal piercing mechanism 170 within in a blister 100 suitable for containing, storing, and dispensing a precise sterile quantity of antigen also capable of pricking the skin of a subject during administration to aid in the generation of a diagnostic response. Similar to the device of FIGS. 2A and 2B, the device of FIG. 4B includes a main body 410 and a plunger 420 for manual compression, dispense and abrasion.

Devices employing multiple doses containing internal mechanisms that provide both for internal piercing of the unit dose form laminate in order to expel its contents to the exterior that also are tipped with one or more sharpened or angled points or protrusions may be arrayed into multi-dose devices that are either single use or reloadable or reusable. In one such embodiment (FIG. 5), multiple, separate unit doses 100, or a cartridge, sheet, or strip of multiple doses containing the internal piercing mechanisms 150 with abrasives tips may be loaded into a device housing 500 that can be applied to a subject such that multiple antigens are transferred to a subject in a single operation or administration. FIG. 5B provides a blow up of one dose of the multiple dispense device of FIG. 5A that better depicts the blister containing the internal piercing mechanism 150 with the pointed tips 180 all contained within the applicator tip 100.

As mentioned above, the multiple dispense device either with the abrasive tips located on either the internal piercing mechanism as provided for example in FIG. 1B or on the applicator tip as shown for example in FIG. 2A, can be configured for non-manual or assisted means provided by including a electromechanical or pneumatic device. FIG. 6 provides one such exemplary embodiment of a multi-dose device 500 with abrasive tips located on the internal piercing mechanism 110 within the dose blister 100. In this device, a multiple plunger apparatus 610 contacts the blisters 100 within cylindrical housings 630. The two part housing comprising an upper housing 640 and lower housing 650 may be clamped of connected by a snap fit connection, threaded, or rotating clamp as shown as 660. The multiple plungers may be compressed by use of an actuator 620 that may be battery powered electromechanically or pneumatically or by other suitable means of applying force and travel to the plungers.

FIGS. 7A (iso-view) and 7B (cutaway view) provide a further exemplary embodiment whereby the devices may include replaceable applicator tips. In this embodiment, the lower housing 700 may be separated from the upper housing 710 by a snap fit 720 (shown), or may be threaded or other means suitable for separating the two parts. Such a design may be utilized to reduce costs and/or provide for simpler reloading of devices. In one alternative embodiment as shown in FIG. 7, said device may be reloaded with individual or pre-sectioned unit doses thereby replacing the applicator tip and blister. However, the multi-dose or multi-antigen devices given by example by FIGS. 3 and 5 may additionally be configured such that the device is reloadable for subsequent tests on the same or other subjects. Said multi-dose, multi-antigen devices may then be reloaded with a pre-filled array or sheet of individual unit dose forms or blisters containing the antigens or other diagnostic material(s). FIG. 8 provides such an exemplary embodiment whereby the device of FIG. 3A can be fitted with replaceable lower housings 320 which includes the applicator tip, blister and housing to be mated to the upper housing 300 of FIG. 3A. In a similar manner the lower housing of FIG. 5A can be replaced thus making that device reusable as well. These embodiments are particularly useful when the device includes assisted actuation, e.g. electromechanical or pneumatic.

Typical prior art devices rely upon point-of-administration preparation of a device that is usually loaded by dipping one or more prongs or other types of tips into one or more reservoirs of an antigen material. Thus the reservoirs are opened to the atmosphere and consequently prone to loss of potency, and airborne and human-introduced contaminates and errors due to mishandling and misapplication of the antigens to the subject. Other devices that are capsule based are similarly filled or prepared at the time of administration and/or rely on dipping or capillary filled channels for the antigen dosing. Such methods are similarly prone to contamination, handing errors, and imprecise and poorly reproducible dosing. To reduce time on task, errors and mistakes, current and prior art devices typically require highly trained technicians to administer the tests following exacting and precise protocols and procedures. The present disclosure thus provides a means of obtaining consistent, sterile allergy testing results in less time that are also robust and more resistant to variations of technician experience and skill at following administration protocol standards.

The invention provided herein thus discloses novel devices that provide for pre-packaged, or Point-of-Use prepared, fully self-contained, sterile devices for precisely delivering a predetermined precise quantity of individual or multiple antigens to a human or on-human subject for the purposes of allergy testing or diagnostics to the skin.

Importantly, the aforementioned and following embodiments are merely for the purposes of illustrating the invention enclosed herein with the knowledge that various design aspects are available to one of ordinary skill in the art of medical device design having the benefit of this disclosure.

The invention claimed is:

1. A device for the storing and dispensing of one or more predetermined sterile quantities of testing or diagnostic material to the skin of a human or non-human subject, comprising:
    a unit dosage form comprising a crushable ampoule or blister comprising an internal volume, a pierceable membrane, a piercing mechanism within the internal volume, and containing the antigen or other fluid or material for testing on a subject;
    wherein the piercing mechanism further comprises an internal channel to allow communication of the unit dosage form contents to the exterior of the unit dosage form and to the skin of a subject,
    a housing fitted with a unit dosage form, a trigger device, comprising one of or combination of a lever, ramp, plunger, cam, plate suitable for transferring force to the unit dosage form such that a crushing force is applied to the unit dosage form to cause the unit dosage form to compress and the piercing mechanism to penetrate the pierceable membrane and discharge the antigen or other fluid or material through the internal channel and contacts the skin of a subject, and
    wherein the housing further comprises an elongated applicator tip further comprising one or more sharpened or angled points for the abrasion, piercing, or puncturing of the skin of a subject.

2. The device of claim 1 wherein the triggering device further comprises an electromechanical or pneumatic actuator.

3. The device of claim 1 wherein said housing is configured such that more than one or an array of multiple unit dosage forms can be loaded into the device and administered substantially simultaneously or by predetermined sequence.

4. The of device of claim 1 wherein the housing is modular such that the one or more applicator tip or tips can be removed and replaced with at least one new applicators tip, thus reusing a portion of the housing.

5. A device for the storing and dispensing of one or more predetermined sterile quantities of testing or diagnostic material to the skin of a human or non-human subject, comprising:
    a unit dosage form comprising a crushable ampoule or blister comprising an internal volume, a pierceable membrane, a piercing mechanism within the internal volume, and containing the antigen or other fluid or material for testing on a subject;
    wherein the piercing mechanism further comprises an internal channel to allow communication of the unit dosage form contents to the exterior of the unit dosage form and to the skin of a subject, and
    wherein the piercing mechanism further comprises a tip with more than one sharpened or angled points to provide for the abrasion, piercing, puncturing, or disturbance of the skin of a subject.

6. The device of claim 5 further comprising a housing fitted with a unit dosage form comprising a trigger device further comprising one of or combination of a lever, ramp, plunger, cam, plate suitable for transferring force to the unit dosage form such that a crushing force is applied to the unit dosage form to cause the unit dosage form to compress and the piercing mechanism to penetrate the pierceable membrane and discharge the antigen or other fluid or material through the internal channel and contacts the skin of a subject.

7. The device of claim 6 wherein the triggering device further comprises an electromechanical or pneumatic actuator.

8. The device of claim 6 where the said housing is configured such that an array of multiple unit dosage forms can be loaded into the device and administered substantially simultaneously or by predetermined sequence.

* * * * *